United States Patent
Trachtenberg

[11] Patent Number: 6,064,914
[45] Date of Patent: May 16, 2000

[54] THERMOTHERAPY METHOD

[76] Inventor: John R. Trachtenberg, 5 Old Forest Hill Drive, Toronto, Ontario, Canada, M5P2P6

[21] Appl. No.: 09/053,477

[22] Filed: Apr. 1, 1998

Related U.S. Application Data

[60] Provisional application No. 60/076,619, Mar. 3, 1998.

[51] Int. Cl.[7] .................................................. A61F 2/00
[52] U.S. Cl. .............................. 607/102; 606/42; 607/113
[58] Field of Search ................................. 607/100–102, 607/113, 115–116, 154–156; 606/41–42, 192

[56] References Cited

U.S. PATENT DOCUMENTS

| | | |
|---|---|---|
| 5,234,004 | 8/1993 | Hascoet et al. ............................ 607/116 |
| 5,354,325 | 10/1994 | Chive et al. ............................... 607/101 |
| 5,404,881 | 4/1995 | Cathaud et al. . |
| 5,575,811 | 11/1996 | Reid et al. ................................ 607/101 |
| 5,620,479 | 4/1997 | Diederich ................................... 607/97 |
| 5,683,382 | 11/1997 | Lenihan et al. ............................ 606/33 |
| 5,733,316 | 3/1998 | Tierney et al. ........................... 607/101 |
| 5,807,395 | 9/1998 | Mulier et al. .............................. 606/41 |

*Primary Examiner*—John P. Leubecker
*Assistant Examiner*—Roy Gibson
*Attorney, Agent, or Firm*—Kohn & Associates

[57] ABSTRACT

A hydrodissection apparatus for treatment of the prostate of a patient using a moving apparatus for moving the prostate away from the adjacent rectum and using heat to heat the prostate while keeping the rectum protected from any damage that could be caused by the heat.

3 Claims, 2 Drawing Sheets

THERMOTHERAPY METHOD

CROSSREFERENCE TO RELATED APPLICATIONS

This application claims benefit of Provisional application Ser. No. 60/076,619 filed Mar. 3, 1998.

GOVERNMENT SUPPORT

Not Applicable

BACKGROUND OF THE INVENTION

FIELD OF THE INVENTION

The present invention relates generally to an apparatus and method for performing a thermal therapy patient treatment protocol. More particularly, the invention relates to a novel apparatus and method for physically separating organs to enable aggressive thermal therapy to be administered safely and relatively comfortably, on an outpatient basis, if desired.

Thermal therapy has been proven to be an effective method of treating various human tissues. Thermal therapy includes tissue freezing, thermotherapy, hyperthermia treatment and various cooling treatments. Thermotherapy treatment is a relatively new method of treating cancerous, diseased and/or undesirably enlarged human prostate tissues. Hyperthermia treatment is well known in the art, involving the maintaining of a temperature between 41.5 degrees Celsius through 45 degrees Celsius. Thermotherapy, on the other hand, usually requires energy application to achieve a temperature above 45 degrees Celsius for the purposes of coagulating the target tissue. Tissue coagulation beneficially changes the density of the tissue. As the tissue shrinks, forms scars and is reabsorbed, the impingement of the enlarged tissues, such as an abnormal prostate, is substantially lessened. Further, tissue coagulation and its beneficial effects are useful for treating cancerous tissue, because cancer cells are particularly susceptible to abnormal temperatures. Cancer cells can be treated in accordance with the present invention with temperatures in excess of 100 degrees Celsius without damage to the therapy applicator or discomfort to the patient.

The higher temperatures required by thermotherapy require delivery of larger amounts of energy to the target prostate tissues. At the same time, it is important to protect nontarget tissues from the high thermotherapy temperatures used in the treatment. Providing safe and effective thermal therapy, therefore, requires devices and methods which have further capabilities compared to those which are suitable for hyperthermia.

Although devices and methods for treating prostate cancer and benign prostatic hyperplasia have evolved dramatically in recent years, significant improvements have not occurred and such progress is badly needed. As recently as 1983, medical textbooks recommended surgery for removing cancerous or impinging prostatic tissues and four different surgical techniques were utilized. Suprapubic prostatectomy was a recommended method of removing the prostate tissue through an abdominal wound. Significant blood loss and the concomitant hazards of any major surgical procedure were possible with this approach.

Perineal prostatectomy was an alternatively recommended surgical procedure which involved gland removal through a relatively large incision in the perineum. Infection, incontinence, impotence or rectal injury were more likely with this method than with alternative surgical procedures.

Transurethral resection of the prostate gland has been another recommended method of treating benign prostatic hyperplasia. This method required inserting a rigid tube into the urethra 15. A loop of wire connected with electrical current was rotated in the tube to remove shavings of the prostate at the bladder orifice. In this way, no incision was needed. However, strictures were more frequent and repeat operations were sometimes necessary.

The other recommended surgical technique for treatment of benign prostatic hyperplasia was retropubic prostatectomy. This required a lower abdominal incision through which the prostate gland was removed. Blood loss was more easily controlled with this method, but inflammation of the pubic bone was more likely.

With the above surgical techniques, the medical textbooks noted the vascularity of the hyperplastic prostate gland and the corresponding dangers of substantial blood loss and shock. Careful medical attention was necessary following these medical procedures.

The problems previously described led medical researchers to develop alternative methods for treating prostate cancer and benign prostatic hyperplasia. Researchers began to incorporate heat sources in Foley catheters after discovering that enlarged mammalian tissues responded favorably to increased temperatures. Examples of devices directed to treatment of prostate tissue include U.S. Pat. No. 4,662,383 (Harada), U.S. Pat. No. 4,967,765 (Turner), U.S. Pat. No. 4,662,383 (Sogawa) and German Patent No. DE 2407559 C3 (Dreyer). Though these references disclosed structures which embodied improvements over the surgical techniques, significant problems still remain unsolved.

Recent research has indicated that cancerous and/or enlarged prostate glands are most effectively treated with higher temperatures than previously thought. Complete utilization of this discovery has been tempered by difficulties in protecting rectal wall tissues from thermally induced damage. While shielding has been addressed in some hyperthermia prior art devices, the higher energy field intensities associated with thermotherapy necessitate devices and methods having further capabilities beyond those suitable for hyperthermia. For example, the microwave-based devices disclosed in the above-referenced patents have generally produced relatively uniform cylindrical energy fields. Even at the lower energy field intensities encountered in hyperthermia treatment, unacceptably high rectal wall temperatures have limited treatment periods and effectiveness.

The prostate lies immediately above the rectum. The two structures are separated only by a thin fascial plane called the Denonvillier's fascia. This is composed of two layers which are in close contact. To kill prostate cancer cells within the prostate, the entire prostate, including the peripheral zone, must be included in the thermal window. However, because the rectum lies in intimate contact with the prostate, if one were to direct enough noxious agents, in most methods heat, to the periphery of the prostate sufficient to kill the cancer cells, one risks additionally damaging the adjacent rectum. This is the problem that the previously known methods have, which leads either to failure of treatment or morbidity.

In addition, efficient and selective cooling (for heat-based treatments) or warming (for freezing treatments) of the devices is rarely provided. This substantially increases patient discomfort and increases the likelihood of healthy tissue damage during benign prostatic hyperplasia treatments. These problems have necessitated complex and expensive temperature monitoring systems along the urethral wall. Satisfactory ablative prostate cancer therapy using extremely high or low temperature treatments cannot be undertaken without effective thermal control of the therapy device including effective cooling of exterior portions of the therapy device.

It would therefore be useful to utilize a method of treatment which enables the physician to both protect the adjacent rectum while still enabling the physician to direct enough heat to sufficiently kill the cancer cells.

SUMMARY OF THE INVENTION

According to the present invention, a hydrodissection apparatus is utilized for treating the prostate of a patient by moving the prostate away from the rectum and then applying sufficient heat to the prostate to kill the cancer cells while protecting the rectum. Also included in the present application is a method of treating the prostate of a patient using the apparatus. Further included is a method of providing thermal therapy to prostate tissue of a patient by providing a fluid flow which thereby causes a physical separation of the prostate from the rectum.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
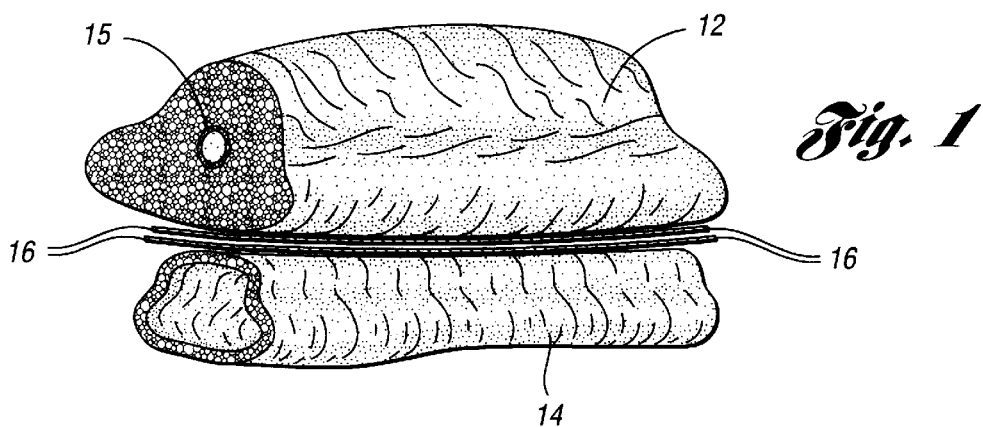
FIG. 1 illustrates a front view of a human prostate and rectum in accordance with conventional medical knowledge.
Figure 2:
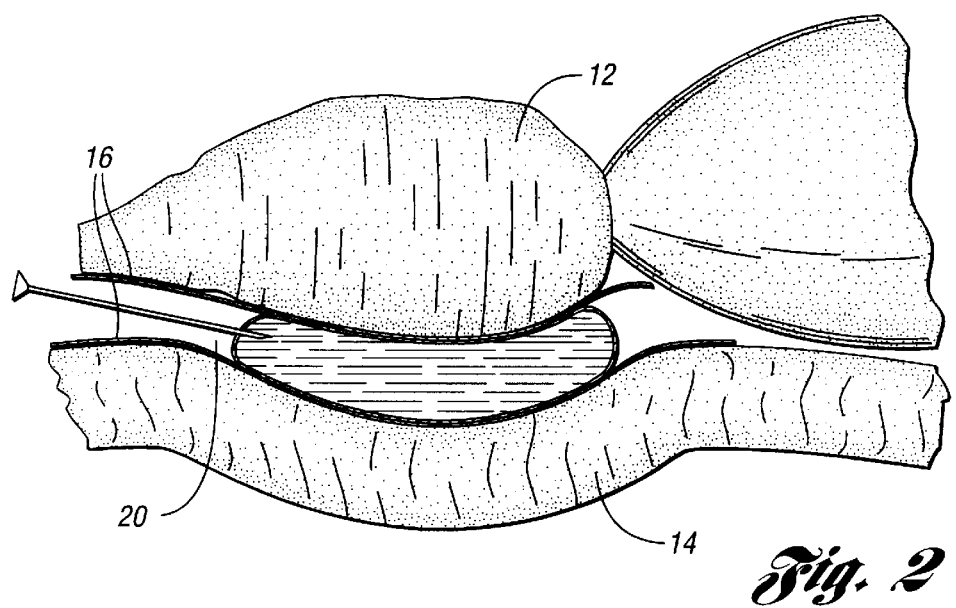
FIG. 2 shows a front view of the prostate and rectum of FIG. 1 physically separated by a fluid.
Figure 3:
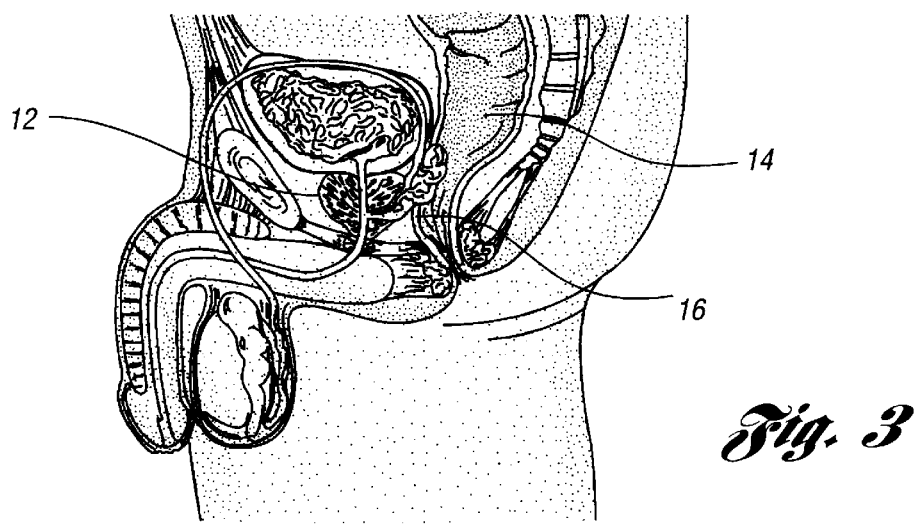
FIG. 3 illustrates a side view of a prostate and rectum physically separated by a fluid.
Figure 4:
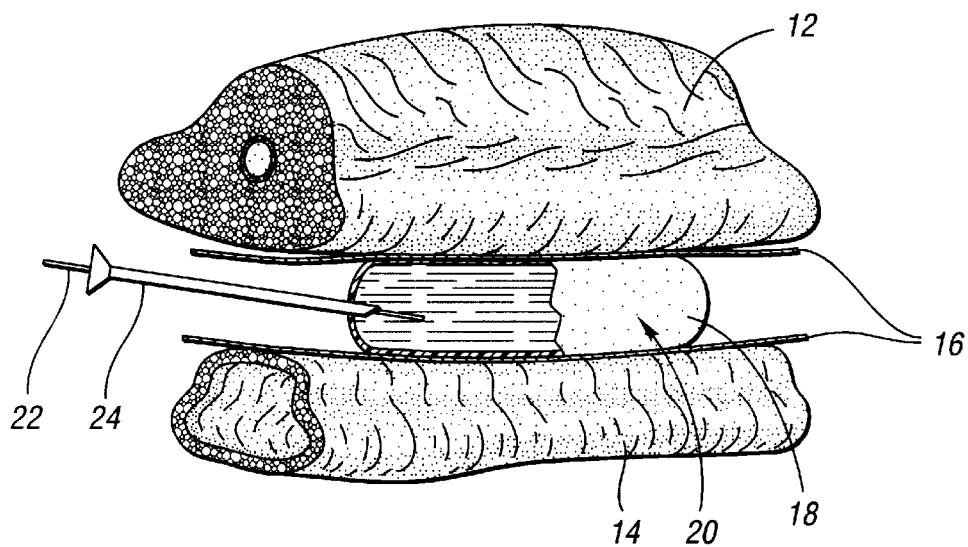
FIG. 4 shows a front view of the prostate and rectum of FIG. 2 showing a device for providing the fluid and a fluid temperature sensor.
Figure 5:
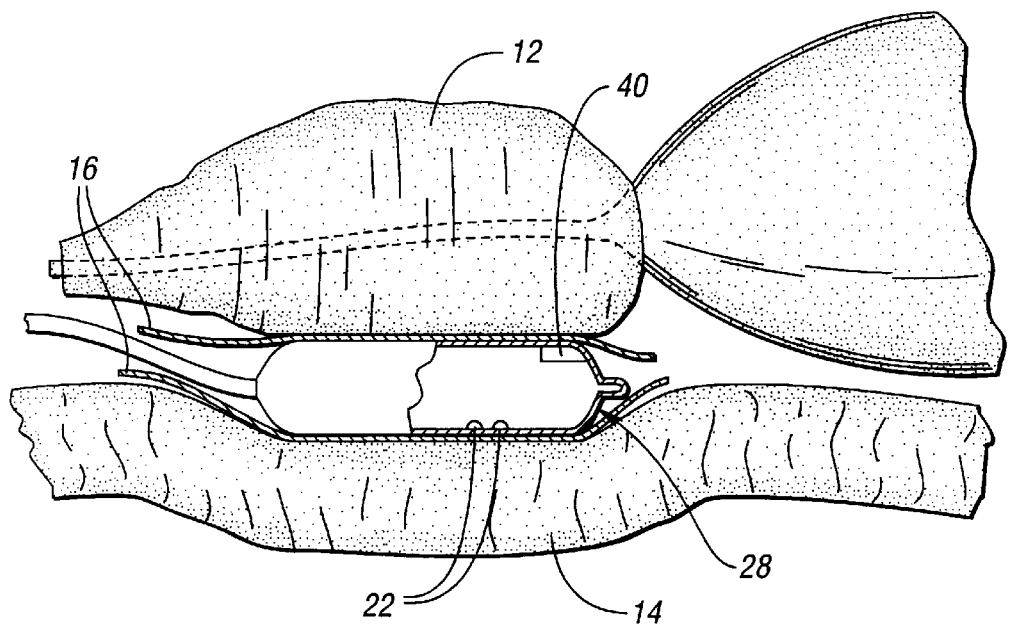
FIG. 5 shows a front view of a delivery system constructed in accordance with one form of the invention.

FIG. 1 illustrates a front view of a human prostate 12 located immediately above a human rectum 14 in accordance with well-known anatomical observations. The prostate and the rectum 14 are separated by a thin fascial plane called "Denonviller's fascia" or a "biplane fascial layer" 16. Denonviller's fascia is composed of two layers of fibrous membrane tissue in close contact. To kill prostatic cancer cells within the prostate 12, the entire prostate 12 must typically be subjected to the thermal therapy, regardless of whether heating or cooling techniques are utilized. Because the rectum 14 naturally lies in intimate contact with the prostate 12 and the biplane fascial layer 16, if one subjects the periphery of the prostate 12 to intense thermal therapy to kill all living tissue within, one risks damaging the portions of the rectum 14 close to the prostate 12. Such damage can lead to severe complications such as urethral or vasicle-rectal fistulae.

The present invention can use ultrasound or magnetic resonance or other imaging modalities to direct the percutaneous (through trans-perineal techniques or others) instillation of fluid flow 18 under pressure into the biplane fascial layer 16 (Denonvillier's fascia) to create a real space 20 from the pre-existing virtual space, thereby physically separating the rectum 14 from the prostate 12. Extremely low fluid pressures (i.e., gravity-fed flows) can be used in accordance with the invention if desired. The fluid flow 18 tracks into this fascial plane, physically and thermally isolating the rectum 14 from the prostate 12, and isolating the prostate 12 from lateral and inferior lying structures (e.g., the perineal diaphragm, sphincteric mechanism and neurovascular bundles). Fluid flow 18 can be continuously instilled to cool (or warm, as desired) and separate this space 20 and protect adjacent structures. Thermoprobes can be placed into the periphery of the prostate to ensure adequate temperatures to ablate cancer cells while temperature sensors 22 and pressure monitors in the fluid space can dictate the amount of fluid flow necessary to adequately protect adjacent structures. Conventional intermittent trans-rectal ultrasound can also help ensure adequate continuing separation of vital tissues by the instilled cooling fluid flow 18.

In accordance with one preferred embodiment of the invention, a needle 24 is inserted at a location near or between the prostate 12 and rectum 14 to infuse a fluid flow 18 for cleaving or providing a space 20 physically separating the prostate 12 and rectum 14. It will be apparent that all of the organ separation methods described herein can be practiced from a variety of entry ports: transperineally, transrectally, transurethrally, suprapubically and others. The fluid flow 18 can be a cooling solution (ionic or nonionic), an insulating medium (as in energy absorption), an energy reflecting medium for use with some trans-urethral therapy applications, a warming solution, air or a gas, or some type of gel. Infusing these types of agents essentially provides a space 20 to either help insulate the rectum 14 from the therapy or can provide a means to either augment the therapy or to provide the actual therapy itself.

The fluid flow 18 can be bolused in or continuously infused to provide proper maintenance of the space 20 between the organs and proper temperature of the fluid flow 18. The fluid flow 18 can also be recirculated into and out of the space 20 by the use of a multilumen catheter or by use of multiple catheters. For heat treatments, the fluid flow 18 can be cooled to provide cooling to the rectum 14. Alternatively, the fluid flow 18 can be maintained at a minimally therapeutic temperature. Therefore, monitoring of the fluid flow 18 temperature within the space 20 or in the delivered and returned solution temperature can be used to guide or enhance the treatment effectiveness. For cooling or freezing treatments of the prostate 12, the fluid flow 18 can be warmed to ensure that the rectum 14 is provided a safety cushion such that the therapy inside the prostate 12 can be as aggressive as possible.

This space 20, once created, can also be used to provide a window within which to now deliver therapy, feedback regarding the extent of the treatment by providing more localized control or for various types of imaging (e.g., ultrasound). Further details for implementing those functionalities are described hereinbelow. This technique can be especially useful for prostate cancer which develops predominantly in the posterior and lateral edges of the prostate 12. The close proximity of the thermally sensitive rectum 14 to those commonly afflicted areas of the prostate 12 limits the effectiveness of conventional treatments. By utilizing the space 20 or window to now provide a means for directly treating these regions of the prostate 12 in a directional way, the rectum 14 can be protected from thermal damage, and the location of the cancer can be extremely aggressively treated in a safe and relatively comfortable manner. Therapy elements (energy sources) capable of providing desirably asymmetric energy patterns include, without limitation, laser, microwave (especially with some type of shielding (e.g., air) to avoid heating the rectum 14), cryosurgery, ultrasound (focused or diffuse) and diagnostic ultrasound. The diagnostic ultrasound and the therapeutic ultrasound can be combined into the same probe if desired.

The therapeutic element 36 can be directional, shielded or simply conventional. The element 36 can then be used to effectively treat the outer portions of the prostate 12. This approach can be used in conjunction with another form of treatment, either drug or device, and can be used with interstitial or intraluminal treatments. If needed, a conventional endoscope or similar device can be inserted to guide the application of the treatment under direct visualization.

The therapeutic element 36 can incorporate a locating means 40 whereby the location of the treatment can be confirmed, adjusted or maintained throughout the treatment. This locating means 40 can include, without limitation, a helium neon laser pointer for direct vision or a mechanical/ultrasound opaque (i.e., metal) indicator on the probe itself. It can also comprise an ultrasound imaging device capable of monitoring the therapeutic effect in the tissue itself.

While prostate treatment uses of the present invention are described herein for illustrative purposes, it will be readily apparent that the present invention can also be used to treat other anatomical structures including, without limitation, structures inherent or attached to the rectum 14 itself (e.g., treating the wall of the rectum 14 or tumors associated with the rectum 14).

Thermal therapy delivery systems 50 can also be used as mechanical separators 28. The delivery system 50 can take a number of forms, such as the one described in copending U.S. patent application Ser. No. 07/976,232, the Detailed Description of Preferred Embodiments which is incorporated herein in its entirety. The delivery system 50 can include the ability to provide degassed and temperature regulated water flow into the delivery system 50 adjacent tissue to be treated. An example of such a suitable delivery system 50 is a single or multiple lumen device which circulates fluid, gas, gel and the like under pressure within a closed environment. The delivery system 50 is intended to be inserted into body cavities or interstitially. The delivery system 50 can be inserted into the body (organ) targeting a specific treatment site. The delivery system 50 can house a therapeutic element 36 such as laser, microwave, therapeutic or diagnostic ultrasound or simply a temperature sensor 22. The fluid flow 18 or infused agent can be recirculated under pressure or can remain static. This form of the invention can deliver therapeutic energy to internal body structures through a minimally invasive procedure.

The delivery system 50 is preferably small in diameter, being 9 French and under. Delivery systems 50 as small as 6 French have been used satisfactorily and are being further miniaturized. The delivery system 50 incorporates 360 degree radial cooling (or warming) which is essential for this intensive thermal therapy, especially for interstitial therapy, because it greatly reduces the potential for exit wounds which could result from both thermal or freezing technologies.

The delivery system 50 can be made out of extremely thin polymers, such as PET, which permits the use of very thin wall thicknesses, thereby minimizing the overall device size. This type of material is essentially nondistensible and can withstand high pressures without failure. This permits passage of fluid flow 18 or other media under pressure to provide flow without compromise of the structure. The delivery system 50 can also be made from typical catheter material with the size increasing due to the need for larger wall thicknesses.

The delivery system 50 can have a rigid structure that aids in insertion or could be made so thin that it essentially has no rigidity. The latter design can be inflated to provide the handling and insertion stability required. This has the advantage of permitting extremely thin wall thicknesses to be used, thereby maximizing throughput flow and/or minimizing overall size. The rigidity of the delivery system 50 can also be used in conjunction with a conventional sharpened tip at one end of the delivery system 50. The sharpened tip enables interstitial insertion of the delivery system 50.

The circulating fluid flow 18 could be either a cooling agent or a warming agent, whichever is required for the particular thermal therapy being utilized. For example, microwave therapy benefits from a cooled device whereby the cooling of the antenna provides a substantial increase in efficiency. The delivery system 50 preferably incorporates the therapeutic elements 36 with complete cooling or warming (via submersion) along the therapeutic element's 36 entire length. This configuration is the most efficient use of space, thereby resulting in a smaller profile.

The outer structure (lumen) 52 of the delivery system 50 can be made either nondistensible or moderately to fully distensible. A distensible outer lumen diameter can be changed even during a treatment to maintain desired contact with the surrounding tissue. This is important for therapies that benefit from intimate contact between the applicator and the tissue for efficient transmission of energy such as microwave, laser, ultrasound and the like.

The change in lumen 52 diameter can be accomplished via an active increase in the internal pressure of the delivery system 50. The pressure can be increased (inflated), decreased or otherwise controlled automatically (or manually) and triggered via the recording of reflected or lost power transmission which can be monitored real time. A conventional pump 60 or other inflation system can be controlled electronically for this purpose. This can be a feedback circuit to improve the efficient transmission of energy throughout the duration of the treatment. In this way, intimate contact between the delivery system 50 and the surrounding tissue can be maintained throughout the treatment, increasing the efficiency of the energy transmission.

Pressurization can also be a useful feature of the delivery system 50 for: clearing the pathway of air or impurities; cooling or warming; and reducing or eliminating modifications in the environment resulting from the treatment. For example, in microwave treatments, the cooling medium is typically a deionized solution such as distilled water. With the application of microwave energy, the microbubbles are produced along the antenna resulting in an increase in reflected power. This can develop into an almost total stoppage of emitted energy into the tissue. Pressurization desirably changes the degassing characteristics of the medium and can minimize the effect of microbubbles out of the energy emitting pathway. Air will block the transmission of most energy sources such as microwave and ultrasound. Laser will also see this as another interface which can result in overheating of the delivery system 50 in that region, possibly resulting in delivery system 50 or laser malfunction. Pressurization can therefore reduce or eliminate reflected power and can be varied throughout a treatment to compensate for changes in the reflected power levels that may occur.

Reflected power will also change according to the matching/mismatching characteristics of the environment surrounding the delivery system 50. This is especially true for microwave energy. Therefore, the measurement of reflected power can be used to correlate with tissue changes in the surrounding tissue. This measurement can, therefore, be used as a feedback mechanism for the progression of a treatment or for a regulating mechanism during a treatment. It can be used as a surrogate measure of tissue temperature or tissue destruction, and can also be used to determine if the treatment is being applied too aggressively. For example, if the therapy is too aggressive, the interface between the delivery system 50 and the surrounding tissue may change (e.g., dehydrate) which will impact the matching between the two entities. The severity of the mismatch will be reflected in an increase in the reflected power. This mismatch clinically results in a less effective administered treatment. By reacting to the change in the reflected power, the aggressiveness of the treatment can be modified to manage this event. Reflected power will change with changes in the temperature of the environment surrounding the delivery system 50. Accordingly, this measure can be used to estimate the temperature of the environment. This is the same for actual physical changes in the surrounding environment (e.g., denaturization, carbonization, dehydration, etc.); therefore, this measure can also estimate effects of a treatment upon the surrounding environment.

While preferred embodiments have been illustrated and described, it should be understood that changes and modifications can be made therein without departing from the invention in its broader aspects. Various features of the invention are defined in the following claims.

The above discussion provides a factual basis for the use of a method of providing thermal therapy to the prostate tissue of a patient. The methods used with and the utility of the present invention can be shown by the following non-limiting examples and accompanying figures.

EXAMPLES
GENERAL METHODS:
Treatment

The patient is administered prophylactic antibiotics on call to the operating room. In the operating room, the patient is placed on the cystoscopy table and a general anesthetic is administered. The suprapubic area and the perineum of the patient is then prepped and draped in the dorsal lithotomy position. The scrotum of the patient is secured to the anterior abdominal wall. The bladder is drained and a 16 French Foley catheter is then placed in the urethra 15. A transrectal ultrasound transducer is then placed in the rectum and the volume and configuration of the prostate 12 is confirmed. The Foley catheter is visualized in the urethra 15 in the sagittal plane.

The position and number of interstitial microwave antenna assemblies (MAA) to be inserted is based upon the volume and configuration of the prostate 12 which will be determined and planned using pretreatment transrectal ultrasound. The actual number of interstitial microwave assemblies (MAA) used will be determined based upon the volume and shape of the gland, as specified below:

45 to 75 cc gland 4 MAA
35 to 45 cc gland 3 MAA
25 to 35 cc gland 2 MAA

The treatment zone locations and number will be determined as to yield complete therapeutic heating of the prostate 12. The sites are plotted on a treatment map during pretreatment planning prior to insertion to achieve efficient isothermic heating of the tissue.

Placement of the intra-prostatic MAA is preceded by repeat topical antibacterial preparation of the perineum. In order to place the MAA, a needle and sheath assembly is first inserted, this assembly is a peel-away assembly. The needle and sheath assembly will be placed transperineally into the left lateral lobe of the prostate 12. The needle will be advanced along an axis 1.5 centimeters away from (as close as medically feasible) and roughly parallel to the prostatic capsule, adjacent to the bladder neck. The position is confirmed using transrectal ultrasound and the needle is repositioned as necessary. The MAA will be inserted into the lumen of the peel-away needle and sheath assembly and advanced until the distal tip reaches the end of the sheath. Proper MAA placement is confirmed when the MAA reaches the sheath hub. The peel-away sheath is then removed, leaving the MAA in place. This procedure is repeated until the predetermined MAA therapy plan has been accomplished. Using a similar technique, a 2-sensor thermosensor array will be inserted at a three or nine o'clock position laterally inside the gland at the capsule. Another 2-sensor array will be placed at the five or seven o'clock position. A single thermosensor array will be placed at the posterior mid line (recto-prostate interface) margins of the prostate 12.

Hydrodissection

The recto-prostatic interface will be delineated by transrectal ultrasound. A needle and sheath assembly will be guided with transrectal ultrasound into this space. The rectum will be separated from the prostate 12 by hydrodissection within the recto-prostatic space. This will be accomplished by inserting a needle and sheath assembly into the recto-prostatic space and connecting a continuous saline solution drip infusion. The hydrodissection will be confirmed by transrectal ultrasound. A single array thermosensor will be inserted via a Y-connector through the needle and sheath assembly into this space. The temperature within the hydrodissection space will be continually monitored. The infusion flow rate will be adjusted to maintain a maximum temperature of 43.5 degrees Celsius within the space. If the monitored temperature rises above 45 degrees Celsius, the flow rate will be increased. If the increased flow rate does not decrease the temperature below 45 degrees, the power of the respective treatment zone(s) will be turned down as described below. A rectal probe with two thermosensors spaced two centimeters apart in length will be placed in the patient's rectum. A transrectal ultrasound transducer with the same two thermosensor array may be used to monitor rectal temperatures and hydrodisection.

A urethral cooling assembly will be coated with sterile lubricant and inserted into the urethra 15 with the anchor balloon inside the urinary bladder. The anchor balloon will be inflated with 7 cc of sterile water and traction will be applied to ensure that the applicator is in the proper position. The proper position will be with the proximal side of the anchor balloon seated against the urinary bladder neck. Either a rectal probe or a transrectal ultrasound transducer will be inserted into the rectum 14. The rectal probe or transrectal ultrasound transducer will have a two sensor thermosensor array spaced by two centimeters. It is preferred to use the transrectal ultrasound transducer/ thermosensor array to visually monitor the hydrodissection space. During the procedure, MAAs, thermosensor fiber arrays, and water connections for the urethral and rectal cooling devices will be attached to the respective system connectors and the treatment program will be initiated.

Power Ramp-Up Procedure

The microwave power will be initiated at 5 watts. The power will be manually increased in 5 watt increments every two minutes to a maximum of 25 watts.

Time: Wattage:
- 0–2 minutes 5 watts
- 2–4 minutes 10 watts
- 4–6 minutes 15 watts
- 5–8 minutes 20 watts
- 8–10 minutes 25 watts The power of the respective treatment zone will be turned down in 2.5 watt increments when the interstitial thermosensor reaches 75 degrees Celsius. The power will be lowered 2.5 watts every one minute until the interstitial temperatures within the respective treatment zone(s) are stabilized within the target treatment temperature range, 55 to 75 degrees Celsius.

The treatment time will start when all interstitial thermosensors have reached the treatment range, 55 to 75 degrees Celsius. A minimum temperature of 55 degrees Celsius must be attained to start the treatment clock. The treatment will be 15 minutes at temperatures within the treatment range. If the treatment range is not attained, the treatment will be 20 minutes in length plus the 10 minute power ramp-up time, or 30 minutes total.

The rectal temperature limit will be 43.5 degrees Celsius as measured on the surface of the cooled rectal probe or ultrasound transducer/thermosensor array. If the rectal temperature limit is exceeded, the power will be decreased as described above.

The target intraprostatic temperature during treatment is 75 degrees Celsius for 15 minutes within the target temperature zone to 0.5 centimeters of the margin of the prostate 12. A gradient of 75 to 45 degrees Celsius within this lateral heating zone of the prostate 12 has been calculated. The target temperature zone is a cylinder of tissue extending the length of the prostate 12, roughly parallel with and centered 0.2 centimeters lateral to the urethra 15, extending outward to the prostatic capsule. The urethral cooling assembly consists of a 9 French catheter which inflates to 18 French during treatment. This assembly constantly circulates 30 degrees Celsius cooled water to cool the urethral mucosa. Similarly, the rectal probe contains two thermosensors in a linear array designed to interrupt the treatment and shut down the microwave power if the rectal mucosa temperature exceeds 43.5 degrees Celsius. Additionally, the operator will be alerted via a "pop-up" dialogue box on the treatment screen prior to interruption of treatment. The rectal probe is cooling and protecting the rectal mucosa. Furthermore, the rectal mucosa has been separated by hydrodissection from direct contact with the heated prostate 12 and the created hydrodissection from direct contact with the heated prostate, and the created hydrodissection space is actively cooled via a saline infusion.

The location and size of the target temperature zone will allow for glandular asymmetry and normal anatomic variation in the angle and curvature of the urethra 15 through the prostate 12. The thermosensor's readings will be visually monitored throughout the therapy treatment. At the moment any of the intra-prostatic thermosensors reach 75 degrees Celsius, the microwave power will be lowered at 2.5 watt increments every one minute until the intra-prostatic temperatures are stabilized within the treatment range, 55 to 75 degrees Celsius. Due to the variable heat transfer rates in tissue, some overshot and lag response in temperature beyond the 75 degree Celsius limit is expected and the operator must take each patient's response characteristics into consideration when adjusting the microwave power levels. If the intra-prostatic temperature continues to fall after the microwave power has been decreased, the procedure described for lowering the power will be reversed to maintain the intra-prostatic temperatures within the treatment range.

Throughout this application, various publications are referenced by author and year. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of treating the prostate of a patient, utilizing a hydrodissection apparatus, comprising the steps of: moving the prostate away from adjacent rectum; treating the prostate, with the rectum being protected from the treatment by a hydrodissection space which is created by inserting a needle and chief assembly into the recto-prostatic space and further connecting said needle and sheath assembly to a fluid flow wherein said fluid flow includes a temperature sensing device for monitoring the temperature within said hydrodissection space and adjusting the fluid flow based upon the temperature within said hydrodissection space and when said temperature sensing device receives a reading greater than 45° C. said fluid rate is increased.

2. The method of claim 1, further including a power controlling device which shuts off power when said fluid flow does not decrease said temperature.

3. The method of claim 2, wherein said power controlling device shuts down in 2.5 watt increments.

* * * * *